United States Patent
Rodriquez et al.

(10) Patent No.: US 7,153,005 B2
(45) Date of Patent: Dec. 26, 2006

(54) AUTOMOTIVE BODY INSPECTION LIGHT SUPPORT SYSTEM

(76) Inventors: David Rodriquez, 508 Bristlecone Dr., Arlington, TX (US) 76018; Cesear A. Borgos, III, 104 Addington Pl., Madison, MS (US) 39110

( * ) Notice: Subject to any disclaimer, the term of this patent is extended or adjusted under 35 U.S.C. 154(b) by 28 days.

(21) Appl. No.: 10/953,961

(22) Filed: Sep. 29, 2004

(65) Prior Publication Data

US 2006/0072326 A1   Apr. 6, 2006

(51) Int. Cl.
*F21V 21/26* (2006.01)
*F21V 21/29* (2006.01)

(52) U.S. Cl. ........................ 362/427; 362/419; 362/431

(58) Field of Classification Search ................ 362/427, 362/457, 425, 422, 418–420, 426, 431, 249, 362/250, 804, 401, 285
See application file for complete search history.

(56) References Cited

U.S. PATENT DOCUMENTS 3,240,925 A * 3/1966 Paschke et al. ................ 362/33

* cited by examiner

*Primary Examiner*—Sandra O'Shea
*Assistant Examiner*—Guiyoung Lee
(74) *Attorney, Agent, or Firm*—Carr LLP

(57) ABSTRACT

A body panel smoothness inspection light support system is provided having a movable joint and a rotatable sliding contact electrical power connection, minimizing the tendency for a power cord to wear or fray.

20 Claims, 8 Drawing Sheets

AUTOMOTIVE BODY INSPECTION LIGHT SUPPORT SYSTEM

FIELD OF THE INVENTION

The present invention relates generally to automotive dent repair tools and more particularly, to a body panel smoothness inspection light support device having a movable joint and a rotatable sliding contact electrical power connection.

DESCRIPTION OF THE RELATED ART

In automotive body dent repair, lights are used to help to locate dents and other defects in body panels, prior, during and after repair to locate imperfections. For example, by placing a fluorescent light adjacent a panel that appears smooth to the naked eye, but has small imperfections, the reflected shape of the light tube from the body panel at a variety of angles will appear warped at the sites of the imperfections, thus tending to reveal to a skilled body work mechanic the locations and extent of such imperfections.

Although the employment of such light inspections are important in all body work, the need to accurately locate dents and imperfections in body panels is particularly important in paintless dent repair, where the body filler and/or sanding used in conventional body repair cannot be employed.

In order to properly position the lighting necessary for such inspections, the lighting fixture should be positionable in many positions and at many angles during the course of a repair. Incident light from many different angles allows an experienced worker to observe dents and other imperfections on the surfaces of cars or trucks by the way light is reflected off of the surface. During the course of a repair project, an inspection light may be positioned and repositioned tens or even hundreds of times.

Commonly, some type of mechanism is used to support the light in a fixed position for a period of time while a repair project is underway. For example, a stand type of support can be used to support a light while a person removes a dent from a body panel of a car or truck. Referring to FIG. 1 of the drawings, the reference numeral 100 generally designates such a conventional, movable support for a light. The support 100 comprises a light 102, a first movable joint 104, a horizontal arm 106, a second movable joint 108, a vertical support 112, a power cord 110, and a support base 114.

In order for the support 100 to maintain a lighting position, the components are interconnected to one another. The support base 114 is rigidly attached orthogonally to one end of the vertical support 112. The vertical support 112 is then rigidly coupled to one end of the second movable joint 108. The second movable joint 108 is then coupled to the horizontal arm 106 at a point along the axis of the horizontal arm 106, allowing for limited angular positioning of the horizontal arm 106. Then, the first movable joint 104 is rigidly coupled coaxially to an end of the horizontal arm 106. The first movable joint 104 is then coupled to the light 102 at a point along the axis of the light 102, allowing for limited angular positioning of the light 102 about another axis. However, neither case permits 360 degree movement about an axis.

The light position is maintained as a result of the position of the movable joints present in the support 100. During use of the light, the work person positions and repositions the light by rotating joints 104 and 106.

Referring to FIGS. 2A and 2B of the drawings, first movable joint 104 comprises a horizontal arm 106, a pitch axle 204, a lower support 206, and the light 102. Generally, the light 102 would be rigidly attached to an end of the vertical support 112 or to an end of the horizontal support arm 106. The lower support 206 is mechanically coupled to the light 102 to allow limited angular rotation about the axis 210. The lower support 206 is mechanically coupled to the horizontal arm 106 to allow limited angular rotation about the pitch axle 204. The horizontal arm 106 can then be rigidly coupled to another component, such as the light 102. However, when the first movable joint 104 is utilized in conjunction with the support 100, the power cord 110 is bent and re-bent at large angles and can be easily damaged. The support 100 is commonly used in applications where the lighting position is frequently changed. For example, when performing paintless dent repair, the lighting position can be changed tens or even hundreds of times for a single vehicle. Due to the frequency of movement, the cord 110 will frequently fray or otherwise become damaged, often where the cord 110 is attached to the light. The damage can cause exposed wire carrying 110 VAC that can be potentially lethal, as well as terminating function of the light. In addition to causing a danger of electrocutions, these short circuits delay the work and can shut off electricity to other areas of the plant, even where the body repair work is not being performed. Even if the light fixture itself can be easily replaced with a spare, it may take some time to locate the affected circuit breaker in the plant, thus delaying the work of many persons in the plant. Furthermore, because the support 100 does not provide a full 360 degrees of possible angular positioning in both axes, the light 102 is restricted in the positions it can take.

Therefore, there is a need for a method and/or apparatus for better coupling a power cord to a support structure and light that addresses at least some of the problems associated with conventional methods and apparatuses for providing inspection lighting. In particular, there is a need for an automotive dent repair inspection light support system that facilitates repetitive, multiple repositioning at any desired angle or position that will minimize the tendency to damage or fray power cords supplying power to the lights.

SUMMARY OF THE INVENTION

In one embodiment, an inspection light support device is provided comprising a first support member rotatably movable with respect to a vertical support about a first axis and having a degree of friction between the first support member and the base that is sufficient to maintain the first support member in a static position against the force of gravity unless intentionally moved to another position by manually applied force and a second support member rotatably movable with respect to the first support member about a second axis by means of a rotatable connection having a first part and a second part. One of the first and second parts includes a plurality of circular contacts insulatedly separated from one another and the other one of the first and second parts includes a plurality of contact elements, each of the contact elements being resiliently urged against one of the circular contacts to establish a sliding electrical connection between them permitting full axial relative rotation between them. The device also includes a first plurality of electrically conductive wires extending from one of either the plurality of circular contacts or the plurality of contact elements to a light, a second plurality of electrically conductive wires extending from the other of the plurality of circular contacts or the plurality of contact elements to a power cord, and a mount for mounting the inspection light to the second support member.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail.

Figure 1:
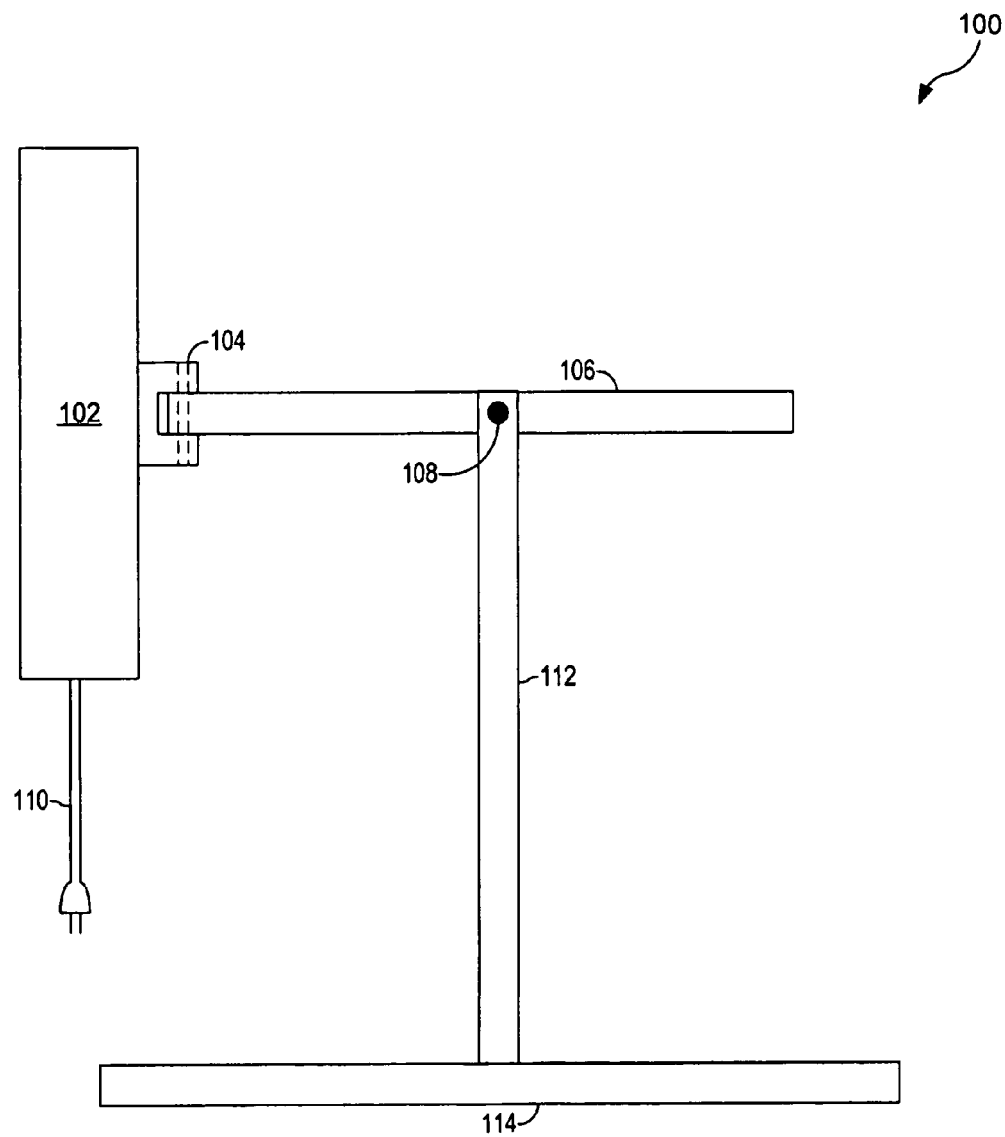
FIG. 1 is an elevation view depicting a conventional light support.
Figure 2A:
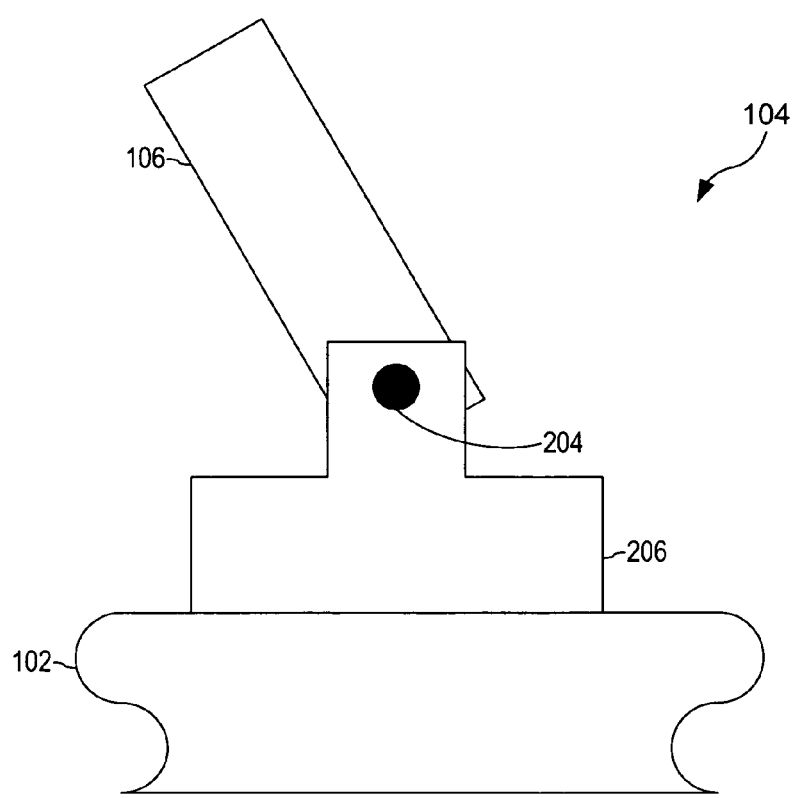
FIGS. 2A and 2B are each side views of a conventional movable joint, each view being orthogonal to the other.
Figure 2B:
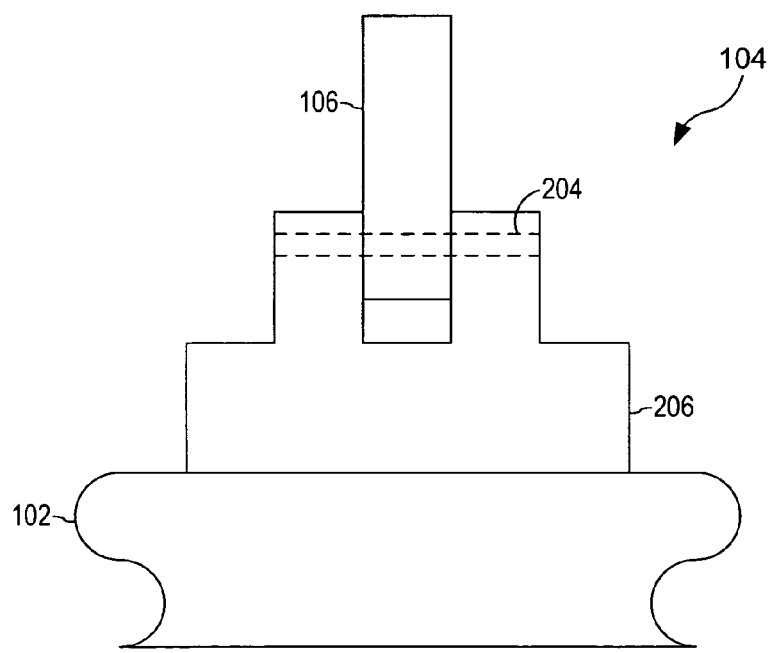
Figure 3:
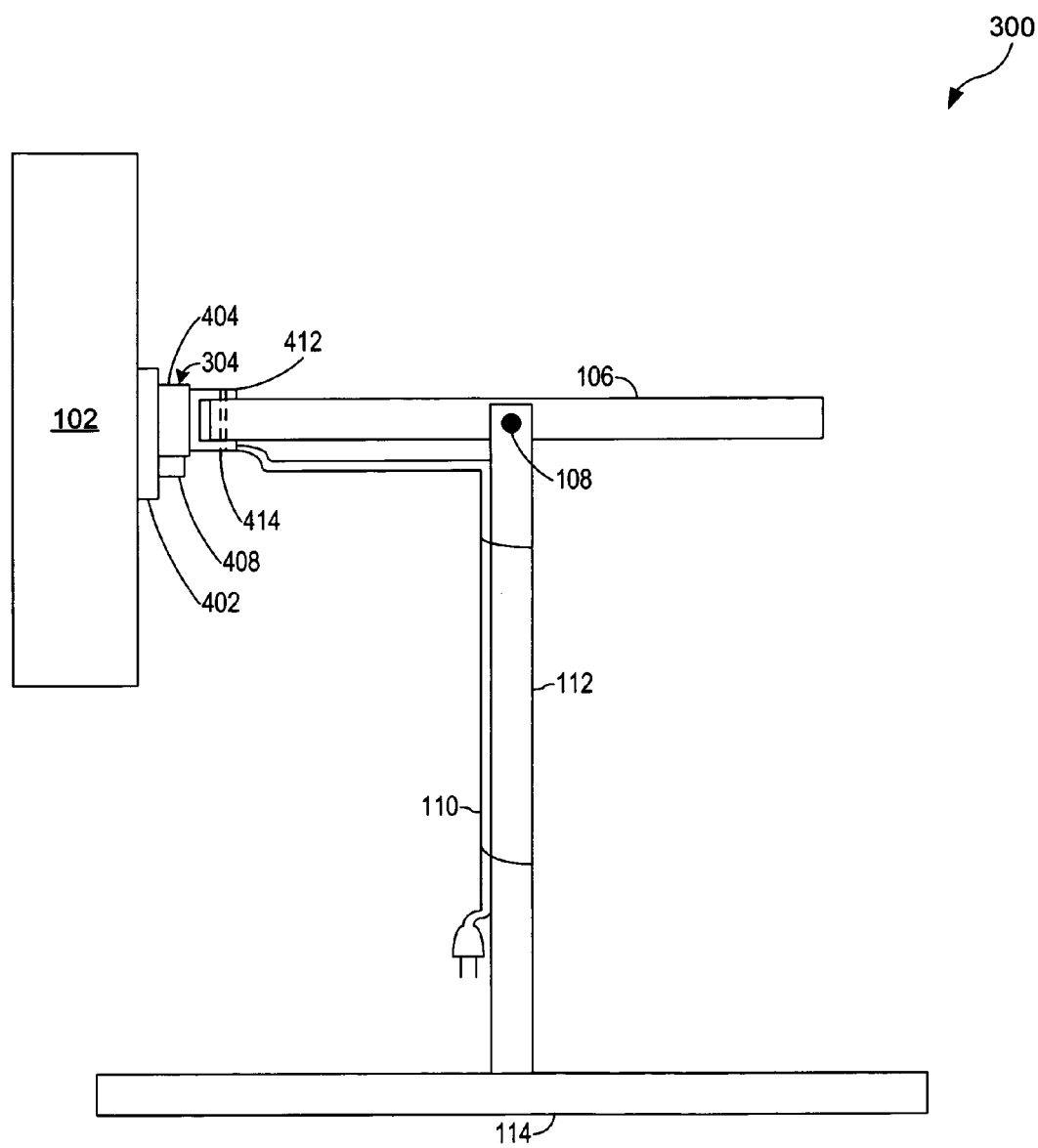
FIG. 3 is an elevation view depicting a light support that utilizes a rotatable joint in accordance with an embodiment of the present invention.

Referring to FIG. 3 of the drawings, the reference numeral 300 generally designates a light support that utilizes a rotatable joint in accordance with an embodiment of the present invention. The support 300 comprises a light 102, a rotatable joint 304, a horizontal arm 106, a universal joint 108, a vertical support 112, a power cord 110, and a support base 114.

In order for the support 300 to maintain a lighting position, the components are interconnected to one another. The support base 114 is attached to one end of the vertical support 112. The vertical support 112 is then coupled to one end of the universal joint 108. The second universal joint 108 is then coupled to the horizontal arm 106 at a point along the axis of the horizontal arm 106, allowing for angular rotation of the horizontal arm 106. Then, the rotatable joint 304 is coupled to an end of the horizontal arm 106. The rotatable joint 304 is then coupled to the light 102 at a point along the middle of the light 102, allowing for angular rotation of the light 102 about two orthogonal axes.

The rotatable joint 304 allows for pitch and azimuthal control of the light 102, while minimizing bending of cord 110 position due to changes in the azimuth and pitch angles. As a result of the constant cord 110 position, the time to damage a cord 110 is dramatically increased. Therefore, overhead costs for body repair could be decreased.

Figure 4A:
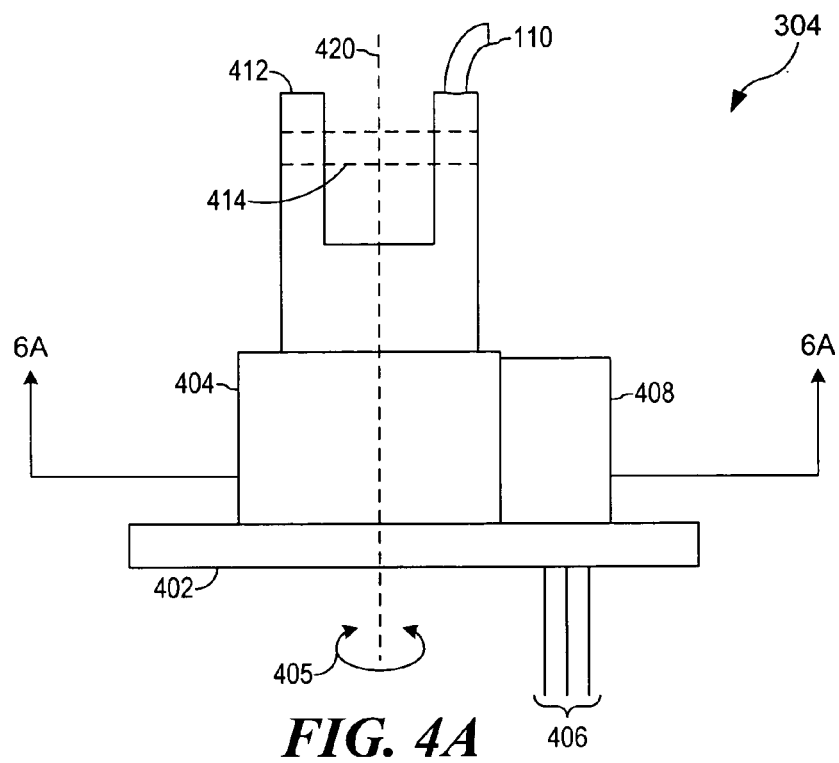
FIGS. 4A and 4B are each side views of the rotatable joint of the light support depicted in FIG. 3, each view being orthogonal to the other.
Figure 4B:
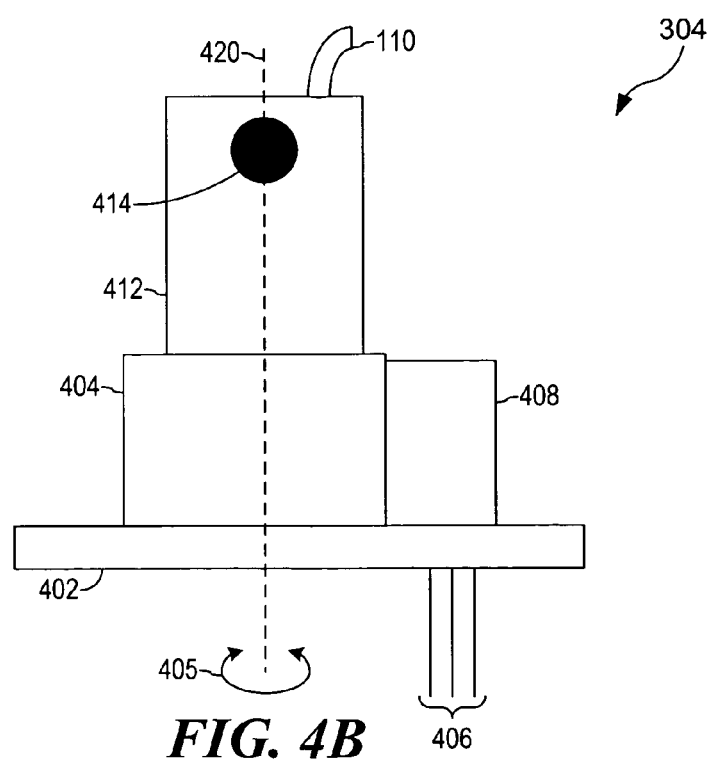

Referring to FIGS. 4A and 4B of the drawings, the joint 304 comprises a rotatable first part 412, a rotatable second part 404, an attachment plate 402, the power cord 110, and an extension 408.

The attachment plate 402 couples the joint 304 to the light 102 of FIG. 3. From there, power wires 406 to the light can protrude from the joint 304 to the light 102. Then, the rotatable second part 404 and the extension 408 are coupled to the attachment plate 402. The power cord 110 is then coupled to the rotatable first part 412, and the rotatable first part 412 is also coupled to the rotatable second part 404. As a result the position and angle angle of the light 102 can be controlled by twistably rotating the rotatable first part 412 with respect to rotatable second part 404 about axis 420. The coefficient of static friction between the rotatable second part 404 and the rotatable first part 412 can be such that the rotatable second part can be moved by the application of a nominal amount of torque (desirably, between about 1 and about 10 ft-lbs) but will remain in a static position otherwise. Pitch control of the light 102 can be achieved by mounting the horizontal arm 106 to the rotatable first part 412 through a pitch axle 414 and by rotating the light about the pitch axle 414. Also, the coefficient of static friction between the horizontal arm 106 and the rotatable first part 412 can be such that horizontal arm 106 can be overcome by the application of a nominal amount of torque (desirably, between about 1 and about 10 ft-lbs), but will remain in a static position otherwise. Alternatively, counterbalancing springs could be used to maintain the parts in a static position when it is not desired to move them.

Figure 5A:
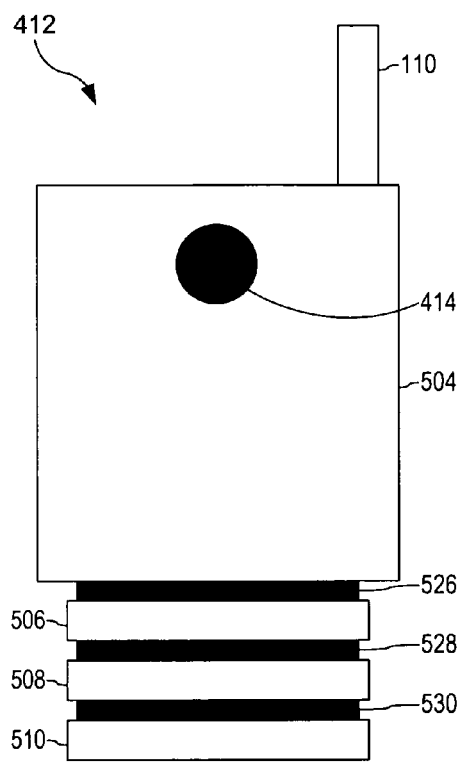
FIGS. 5A, 5B, and 5C are each side views of the rotatable joint of the light support depicted in FIG. 3, FIGS. 5B and 5C of which are orthogonal to the other and FIG. 5A of which shows the same view as FIG. 5B, but is partly in section to reveal in a simplified manner the routing of the power cord conductors to conductive commutator rings on the rotatable joint.
Figure 5B:
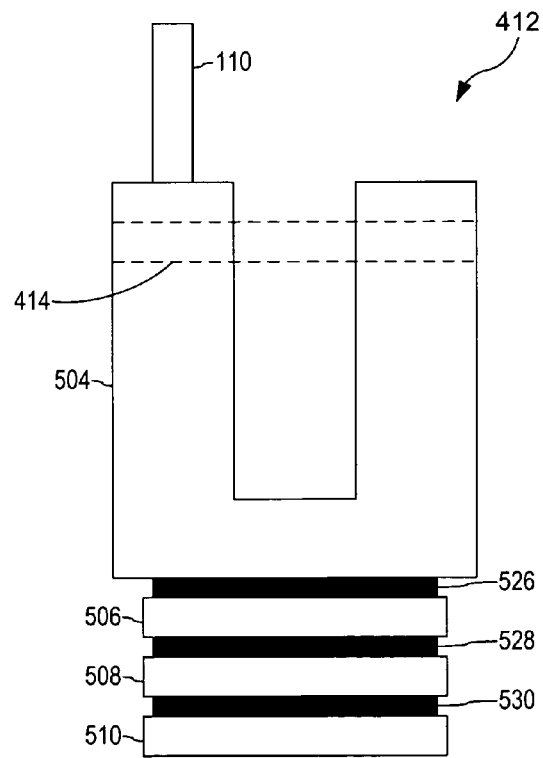
Figure 5C:
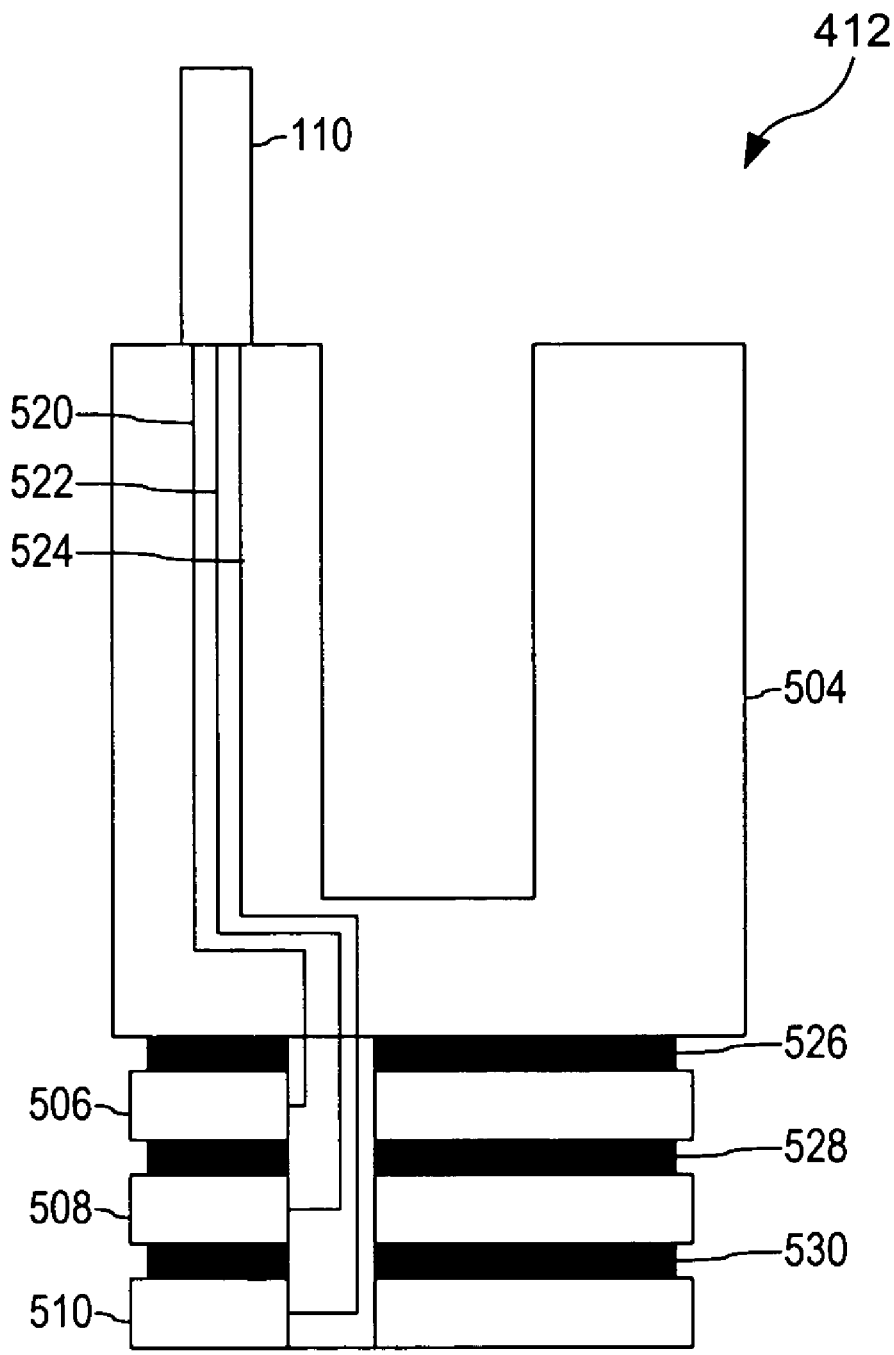

Referring to FIGS. 5A, 5B, and 5C of the drawings, the reference numeral 412 generally designates the rotatable first part including slidable conductor elements permitting power to be supplied to the light while permitting the light to be repositioned in a variety of positions and angles. The rotatable first part comprises a U-coupler 504, a power cord 110, a first insulating ring 526, a first conductor ring 506, a second insulating ring 528, a second conductor ring 508, a third insulator ring 530, and a third conductor ring 510.

The functionality of the rotatable first part 412 occurs by carrying power to the conductive rings. Power can be carried to the rotatable first part 412 through a three-line cord 110, wherein the three lines correspond, respectively, to a hot line, a return line, and a ground line. A portion of rotatable second part 404 configured as a cylindrical bushing (not shown in FIGS. 5A and 5B) protrudes coaxially from the bottom of the U-coupler 504 and is sized so that the conductive rings 506, 508 and 510 rotatably fit inside it. The first insulating ring 526 is mounted over a partially cylindrical support (not shown in FIGS. 5A and 5B) adjacent to the bottom of the U-coupler 504. The first conductive ring 506 is also mounted over the partially cylindrical support (not shown) adjacent to the first insulating ring 526. The second insulating ring 528 is mounted over the partially cylindrical support (not shown) adjacent to the first conductive ring 506. The second conductive ring 508 is mounted over the partially cylindrical support (not shown) immediately adjacent to the second insulating ring 528. The third insulating ring 530 is mounted over the partially cylindrical support (not shown) adjacent to the second conductive ring 508. The third conductive ring 508 is mounted over the partially cylindrical support (not shown) immediately adjacent to the third insulating ring 530. Each of the conductive rings can be composed of brass, copper, aluminum, steel or another metal suited to conduct electricity and capable of withstanding the rigors imposed by friction. The insulating rings are typically composed of a plastic or another material with a low conductivity.

The power cord 520 then carries the power to the rotatable U-coupler 412. The power cord comprises a first power line 520, a second power line 522, and a third power line 524. Each of the three power lines further comprises a copper wire for carrying current. The first power line 520 is coupled to the first conductive ring 506. The second power line 522 is coupled to the second conductive ring 508, and the third power line 523 is coupled to the third conductive ring 510. Each of the respective power lines can be coupled to a conductive ring, through mechanical attachments, such as a bolt, screw, or friction, or may be soldered.

Additionally, for the purposes of safety, the third conducting ring should be attached to the grounded power line. Typically, a washer (not shown) is placed between the rotatable second part 404 of FIG. 4 and the U-coupler 504. The washer (not shown) is usually composed of a metallic alloy, such as steel, because of the durability associated with metallic alloys, like steel. However, metallic washers may conduct electricity to bolts or screws that may be used to secure the joint 304 of FIG. 4. Therefore, the first conductive ring 506 and the second conductive ring would each be individually coupled to either the hot line or the return line.

The feed of electricity from the cord 110 is then further propagated to the light 102 of FIG. 3 through contacts in the attachment plate 402 and extension 408 of FIG. 4. Referring to FIG. 4 of the drawings, the reference numeral 600 generally refers to the lower assembly of the rotatable joint, depicted in greater detail. The lower assembly 600 comprises rotatable second part 404 and the extension 408.

The rotatable second part 404 is the main structural member of the lower assembly 600. The rotatable second part 404 is a notched cylindrical tube, wherein the walls are between approximately one quarter of an inch and three eighths of an inch thick. The extension 408, though, can be a parallelepiped with three distinct cross sections of different sizes, which is then coupled to the rotatable second part 404.

The extension 408 then further comprises a first contact element 608, a second contact element 610, a third contact element 612, a first spring 620, a second spring 622, a third spring 624, a first lead 614, a second lead 616, and a third lead 618. Each of the three contact elements protrudes from one of the surfaces that possess the intermediate cross sectional areas of the three distinct cross sectional areas. Each of the contact elements is composed of a conductive material, such as brass, copper, aluminum, steel or another metal, and which is capable of withstanding the rigors of friction. The first contact element 608 is then coupled to the first spring 620 within the extension 408. The second contact element 610 is coupled to the second spring 622 within the extension 408. The third contact element 612 is coupled to the third spring 624 within the extension 408.

In order to complete the circuit, each of the contacts must contact an electrical lead. The first spring 620 is coupled to the first lead 614. The second spring 622 is coupled to the second lead 616, and the third spring is coupled to the third lead 624. Hence, continuity exists between each of the leads and an electrical lead, so that a power circuit can be completed.

The contact element, too, must also be in a position to contact other conductive material, such as a conductive ring. The extension 408 is placed in the notch of the rotatable second part 404 and coupled to the base. The extension 408 is positioned relative to the rotatable second part 404 so that the contact elements 608, 610, and 612 protrude into a cylindrical cavity created by the rotatable second part 404 and extension 408.

Figure 6A:
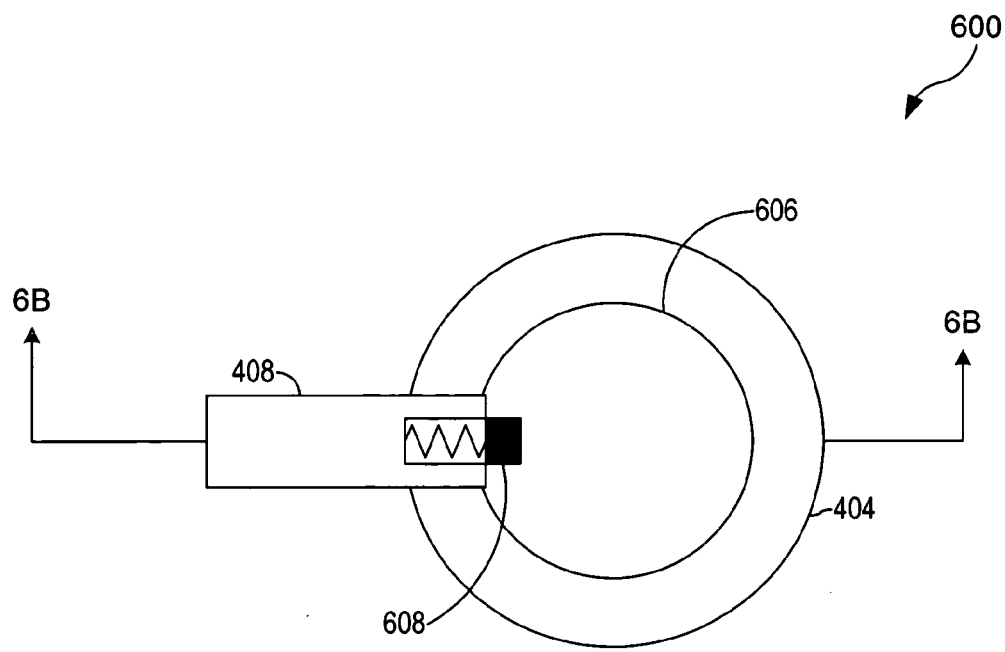
FIG. 6A depicts a section view of the rotatable joint of FIG. 4A, taken along the line 6A, showing resilient contacts of the rotatable joint.
Figure 6B:
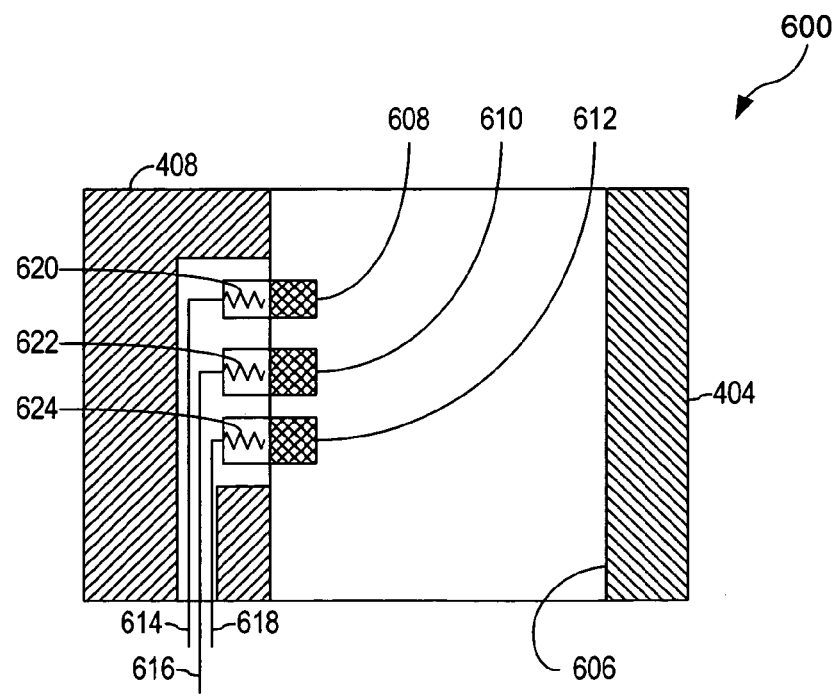
FIG. 6B depicts a section view of the rotatable joint of FIG. 6A, taken along the line 6B, showing resilient contacts of the rotatable joint.

The functionality of the rotatable joint 304 of FIG. 4 is augmented by its combination into the lower assembly 600 of FIG. 6 and the rotatable first part 412 of FIG. 5. The conductive rings 506, 508, and 510, and the attached assembly, are inserted into the cylindrical cavity created by the rotatable second part 404 and the extension 408. Power is carried through the rotatable first part 412 to the conductive rings 506, 508, and 510. Each of the conductive rings 506, 508, and 510 is then in slidable electrical contact with one of the contact elements 608, 610, and 612. Therefore, power can be transferred through the rotatable pitch assembly at any azimuthal position of the rotatable first part 412. Further, 360 degrees of rotation is possible about axis 420 and such rotation can be continued in the same direction an indefinite number of times without requiring untwisting of the power cord.

Figure 7A:
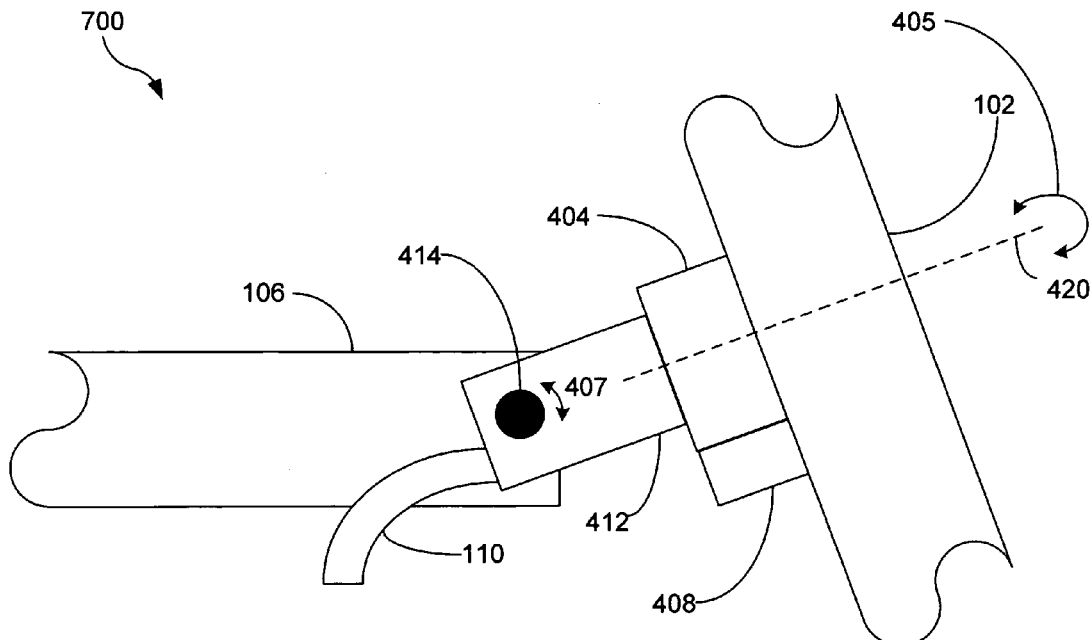
FIG. 7A is an elevation view of the rotatable joint of the light support depicted in FIG. 3, showing the axle coupling the horizontal arm and the rotatable joint.
Figure 7B:
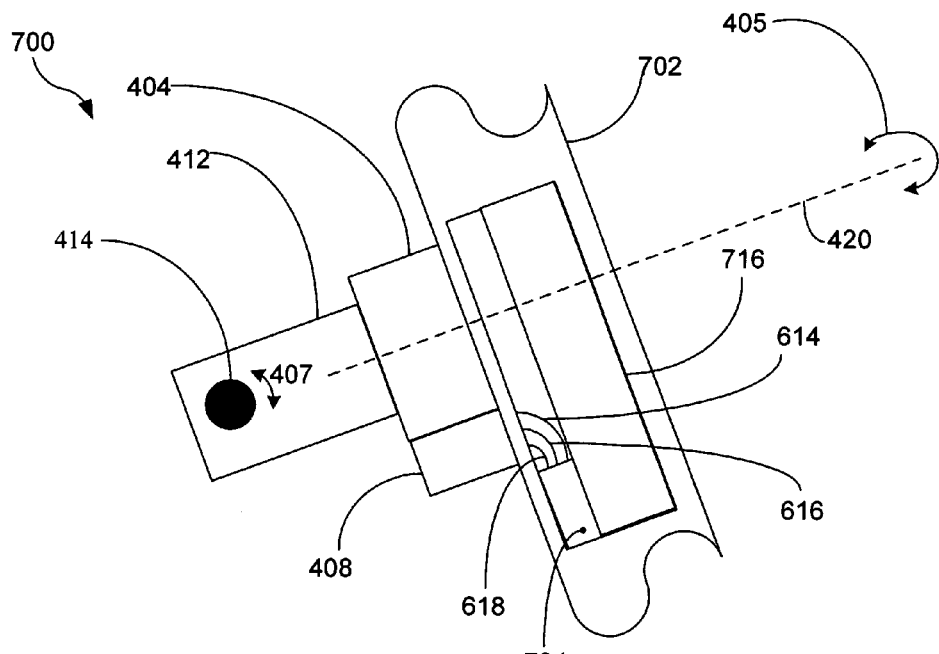
FIG. 7B is an elevation view, partly in cut-away, showing, in a cut-away portion of the light fixture, the routing of the conductive wires from the rotatable joint to the light.

Referring to FIGS. 7A and 7B of the drawings, the reference numeral generally designates an assembly where the rotatable joint couples a horizontal arm and a light together. The assembly 700 comprises a horizontal arm 106, a rotatable first part 412, a rotatable second part 404, a extension 408, a light 702, a pitch axle 414, and a power cord 110.

The horizontal arm 106 is coupled to the rotatable first part 412 by way of the axis 414. That way, the pitch of the support assembly (and light) can be varied with respect to the horizontal arm 106. The rotatable first part 412 is then coupled to the rotatable second part 404 and extension 408. The rotatable second part 404 and the extension 408 are then coupled to the light 702 by means of attachment plate 402.

Power is then transferred to the light 702 from the power cord. The power is first delivered to the rotatable first part 412 through the power cord 110. The rotatable first part 412, the rotatable second part 404, and the extension 408 comprise the rotatable joint that transfers power. Power from the rotatable joint is transferred to a first lead 614, a second lead 616, and a third lead 618, which correspond to the hot line, the return line and the ground line that are normally associated with convention alternating current power transfer. The leads 616, 618, and 724 are then coupled to a power delivery mechanism 724, which typically comprises a transformer and several other components. The power delivery mechanism 724 then provides the proper voltage and current to the light bulb 716. The light bulb 716 is typically a cylindrical florescent bulb.

It should be noted that, although conductive rings 506, 508 and 510 are shown on the rotatable first part 412 and the contacts 608, 610 and 612 on rotatable second part 404, the conductive rings 506, 508 and 510 could also be disposed on rotatable second part 404 and the contacts 608, 610 and 612 disposed on the rotatable first part 412.

As can be seen in FIGS. 7A and 7B, the rotatable second part 404 of the rotatable joint 304 can be angularly twisted about axis 420 back and forth about arc 405 a full 360 degrees in both directions, as well as an unlimited number of rotations in each directions. The support 412 of the rotatable joint 304 can also be angularly repositioned about axle 414 back and forth about arc 407 in a wide range of pitch angles (though not 360 degrees).

As can be seen in FIGS. 3 and 7A, rotation of pitch joint 414 about axle 414 will cause minimal bending of cord 110, despite large angular movements of support 412 about axle 414. This permits multiple repositioning of the inspection light during body work without wearing, fraying or other damage of the electrical power cord and with greatly reduced risks of short circuits or electrocution.

It is understood that the present invention can take many forms and embodiments. Accordingly, several variations may be made in the foregoing without departing from the spirit or the scope of the invention. The capabilities outlined herein allow for the possibility of a variety of programming models. This disclosure should not be read as preferring any particular programming model, but is instead directed to the underlying mechanisms on which these programming models can be built.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of preferred embodiments. Accordingly, it is appropriate that the appended claims be construed broadly and in a manner consistent with the scope of the invention.

The invention claimed is:

1. An inspection light support device comprising,
   a first support member rotatably mounted near the top of an upstanding support, the upstanding support being supported at its bottom by a base, the first support member being rotatably movable with respect to the upstanding support about a first axis and having means between the first support member and the upstanding support that is sufficient for maintaining the first support member in a static generally horizontal position against the force of gravity unless intentionally moved to another position by manually applied force,
   a second support member having a first part rotatably movable with respect to the first support member about a second axis by means of a rotatable connection, the second axis being generally perpendicular to and offset from the first axis and a second part, the first part and the second part having a degree of friction between the first part and the second part that is sufficient to maintain the first part in a static position against the force of gravity unless intentionally moved to another position by manually applied force,
   one of the first and second parts including a plurality of circular contacts insulatedly separated from one another and the other one of the first and second parts including a plurality of contact elements, each of said contact elements being resiliently urged against one of the circular contacts to establish a sliding electrical connection between them permitting full axial relative rotation between them,
   a first plurality of electrically conductive wires extending from one of either the plurality of circular contacts or the plurality of contact elements to a light,
   a second plurality of electrically conductive wires extending from the other of the plurality of circular contacts or the plurality of contact elements to a power cord, and
   an atttachment member for mounting the inspection light to the second support member.

2. The inspection light support device defined in claim 1 wherein said light is an elongated light suitable for inspection of the smoothness of automotive body panels.

3. The automotive body smoothness inspection light support device defined in claim 2, wherein the elongated light is fluorescent.

4. The automotive body smoothness inspection light support device defined in claim 1, wherein the means between the first support member and the upstanding support that is sufficient for maintaining the first support member in a static position against the force of gravity is supplied by friction between the first support member and the upstanding base.

5. The automotive body smoothness inspection light support device defined in claim 1, wherein the means between the first support member and the upstanding support that is sufficient for maintaining the first support member in a static position against the force of gravity includes a counterbalancing spring.

6. The automotive body smoothness inspection light support device defined in claim 1, wherein the power cord has three conductors and terminates in a plug.

7. The automotive body smoothness inspection light support device defined in claim 1, wherein each of the contact elements are elongated and oriented radially toward the circular contacts.

8. The automotive body smoothness inspection light support device defined in claim 1, wherein the first part includes the contact elements and the second part includes the circular contacts.

9. The automotive body smoothness inspection light support device defined in claim 1, wherein the circular contacts are cylindrical contacts.

10. A method of inspecting the smoothness of automotive body panels with an inspection light supported by a support device having
    a first support member rotatably mounted near the top of an upstanding support, the upstanding support being supported at its bottom by a base, the first support member being rotatably movable with respect to the upstanding support about a first axis and having means between the first support member and the upstanding support that is sufficient for maintaining the first support member in a static generally horizontal position against the force of gravity unless intentionally moved to another position by manually applied force,
    a second support member having a first part rotatably movable with respect to the first support member about a second axis by means of a rotatable connection, the second axis being generally perpendicular to and offset from the first axis and a second part, the first part and the second part having a degree of friction between the first part and the second part that is sufficient to maintain the first part in a static position against the force of gravity unless intentionally moved to another position by manually applied force,
    one of the first and second parts including a plurality of circular contacts insulatedly separated from one another and the other one of the first and second parts including a plurality of contact elements, each of said contact elements being resiliently urged against one of the circular contacts to establish a sliding electrical connection between them permitting full axial relative rotation between them,
    a first plurality of electrically conductive wires extending from one of either the plurality of circular contacts or the plurality of contact elements to a light, a second plurality of electrically conductive wires extending from the other of the plurality of circular contacts or the plurality of contact elements to a power cord, and an atttachment member for mounting the inspection light to the second support member, the method comprising the steps of:

positioning the inspection light by rotating the first support member with respect to the upstanding support and by rotating the second part about the first part to a first desired position and repositioning the inspection light by rotating the second part about the first part by at least 360 degrees to a second desired position without causing twisting of the power cord.

11. The method defined in claim 10, wherein the elongated light is fluorescent.

12. The method defined in claim 10, wherein the means between the first support member and the upstanding support that is sufficient for maintaining the first support member in a static position against the force of gravity is supplied by friction between the first support member and the upstanding support.

13. The method defined in claim 10, wherein the means between the first support member and the upstanding support that is sufficient for maintaining the first support member in a static position against the force of gravity includes a counterbalancing spring.

14. The method defined in claim 10, wherein the power cord has three conductors and terminates in a plug.

15. The method defined in claim 10, wherein each of the contact elements are elongated and oriented radially toward the circular contacts.

16. The method defined in claim 10, wherein the first part includes the contact elements and the second part includes the circular contacts.

17. The method defined in claim 10, wherein the circular contacts are cylindrical contacts.

18. The method defined in claim 10, wherein the contact elements are resiliently urged by springs.

19. The inspection light support device defined in claim 10, wherein the contact elements are resiliently urged by springs.

20. The inspection light support system defined in claim 1, wherein said first axis is generally horizontal and said second axis is generally vertical when said first support member is generally horizontal.

* * * * *